United States Patent [19]

Otani et al.

[11] Patent Number: 4,820,869

[45] Date of Patent: Apr. 11, 1989

[54] METHOD FOR THE SEPARATION OF LEUCINE

[75] Inventors: Masaru Otani; Masami Kojima; Toshio Kitahara, all of Kawasaki, Japan

[73] Assignee: Ajinomoto Co., Inc., Tokyo, Japan

[21] Appl. No.: 139,307

[22] Filed: Dec. 29, 1987

[30] Foreign Application Priority Data

Jan. 7, 1987 [JP] Japan .................................. 62-1279

[51] Int. Cl.$^4$ ............................................. C07C 99/12
[52] U.S. Cl. ................................................... 562/554
[58] Field of Search ........................................ 562/554

[56] References Cited

U.S. PATENT DOCUMENTS

| | | | |
|---|---|---|---|
| 3,686,118 | 8/1972 | Benson | 562/554 |
| 3,960,942 | 6/1976 | Hirsbrunner | 562/554 |
| 4,263,450 | 4/1981 | Steinmetzer | 562/554 |
| 4,307,246 | 12/1981 | Bertholet | 562/554 |
| 4,731,476 | 3/1988 | Roos | 562/554 |

*Primary Examiner*—Michael L. Shippen
*Attorney, Agent, or Firm*—Oblon, Fisher, Spivak, McClelland & Maier

[57] ABSTRACT

A method for separating leucine from a mixture of amino acids containing at least leucine and isoleucine, which comprises subjecting an aqueous solution of a mixture of amino acids to centrifugal force, and forcing by the application of pressure a water-saturated organic solvent immiscible with water to pass through the aqueous solution against the centrifugal force, to selectively extract leucine in said water-saturated organic solvent.

4 Claims, 1 Drawing Sheet

METHOD FOR THE SEPARATION OF LEUCINE

BACKGROUND OF THE INVENTION

1. Field of the Invention

The present invention relates to a method for separating leucine from a mixture of amino acids in which both leucine and isoleucine are obtained.

2. Description of the Related Art

Known methods for separating leucine from isoleucine or vice versa include a method in which isoleucine is purified by using methyl ethyl ketone (see Japanese Patent Application (Laid Open) No. 51,440/81), a method wherein a copper or nickel salt is employed (see Japanese Patent Application No. (Laid Open) No. 123,622/75), and a method in which salts of benzenesulfonic acid are utilized (see Japanese Patent Application (Laid Open) No. 149,222/76). In these methods, however, the removal or recovery of solvents or metal salts used is troublesome and costly.

In view of the problems associated with the prior art methods, there has been a need for a new method which makes it possible to separate leucine or isoleucine from a mixture of amino acids containing both leucine and isoleucine, in a convenient manner at a low cost.

The present inventors have conducted intensive investigations with the aim of developing a convenient process for separating leucine from isoleucine or vise versa and, as a result, completed the present invention.

SUMMARY OF THE INVENTION

Accordingly, an object of the present invention is to enable separation of leucine from an amino acid mixture in which at least leucine and isoleucine are contained.

The above object and other objects which will hereinafter become more readily apparent, have been achieved by providing a method for separating leucine from a mixture of amino acids containing at least leucine and isoleucine, which comprises retaining an aqueous solution of a mixture of amino acids by centrifugal force, and forcing by the application of pressure, a water-saturated organic solvent immiscible with water, through the said aqueous solution to extract leucine.

DETAILED DESCRIPTION OF THE PREFERRED EMBODIMENTS

Figure 1:
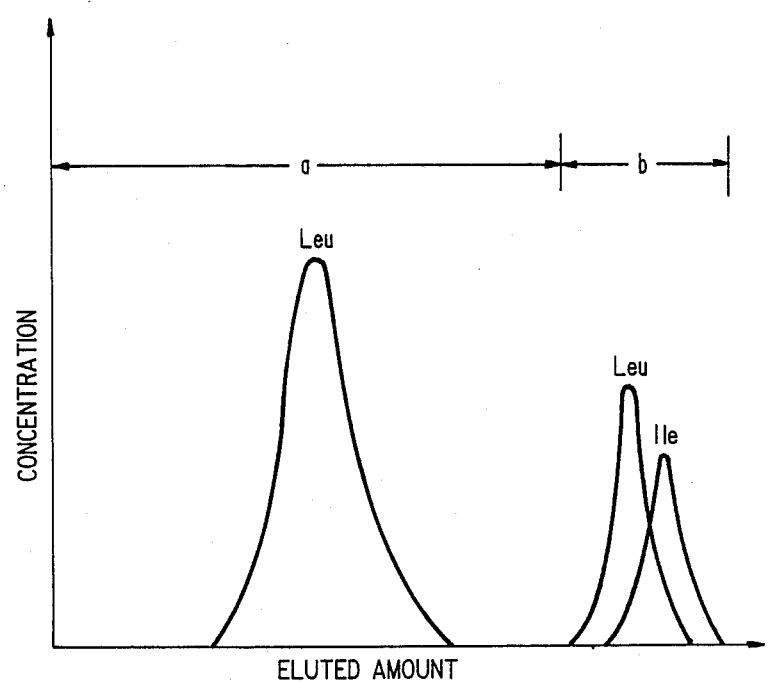
FIG. 1 is a chart showing the results obtained in Example 1.
a: Normal elution
b: Reverse elution

Any mixtures of amino acids containing leucine and isoleucine can be treated by the method of the present invention. Such a mixture may contain other amino acids, as well as other impurities. Thus, the present invention provides a method for separating leucine from a mixture containing leucine and isoleucine, and its object is to make it possible to separate the two amino acids from each other.

In the case where the amino acid mixture is contaminated with amino acids other than leucine and isoleucine and other impurities, part or all of them may become associated with the leucine separated therefrom in accordance with the method of the invention. In such a case, leucine can be purified, if desired, by other means of purification. It is possible to carry out the purification to such a degree that isoleucine is not contained at all in the leucine separated by the present method. In cases where such a high level of purity is not required, the purification can be carried out to such a degree that the percentage of isoleucine contained in the thus separated leucine is, e.g., less than ca. 2%, preferably less than ca. 1%.

The raw material or mixture of amino acids is retained in the state of an aqueous mixture with the application of centrifugal force. A water-saturated organic solvent immiscible with water, such as an alcohol containing 3 to 4 carbon atoms (e.g., isopropanol, n-propanol, n-butanol, sec-butanol, etc., preferably isopropanol or butanol) is passed with application of pressure through the solution against the centrifugal force, to extract leucine or a mixture of amino acids containing leucine. Then, leucine or a mixture of amino acids containing leucine is separated from the extract. Where desired, amino acids other than leucine contained in the thus separated leucine can be separated by repeating the method of the present invention or by applying another purification method to it.

In the method of the present invention, it can be convenient to use a multiple liquid-liquid distribution fractionator, which is a continuous liquid-liquid distributional fractionating device utilizing centrifugal force and is different from the prior counter-current distributional fraction devices and the liquid drop counter-current distribution devices.

Because of the centrifugal force, the device can be more advantageous as a continuous distributional fractionator than other devices.

Explanation will be given hereinbelow on the principle of the device. Distribution tubes are placed on a centrifugal rotor and a mixture of amino acids is charged into the tubes as a stationary phase. A mobile phase of a solvent (e.g., butanol or propanol) is continuously supplied to the liquid of the stationary phase through one end of the axis of the rotor.

With the action of centrifugal force, liquid of the mobile phase passes through the stationary phasae in the form of fine droplets and flows out of the other end of the rotational axis.

The ingredients contained in the sample are fractionated by liquid-liquid distribution during the migration through the stationary phase, and then collected separately.

As stated hereinabove, mixtures of amino acids used as a raw material for the treatment may contain both hydrophobic and hydrophilic amino acids. The mixtures may be a hydrolysate of proteins or an amino acid fermentation liquor with the microbial cells contained in said fermentation liquor removed or a solution prepared by dissolving crystals of crude amino acids.

Explanation will be given hereinbelow on the properties of mixtures of amino acids. The lower the pH value of a mixture or the higher the concentration of salts in a mixture, the greater becomes the distribution coefficient to organic solvents. Accordingly, the extraction can be carried out at a pH of 1 to 3 with the addition of a mineral acid, such as hydrochloric acid, sulfuric acid, etc., so as to increase the solubility of amino acids, in other words, to increase the possible load of amino acids treatable at a time. There are no particular limitations on the concentration of amino acids. However, in the case where a hydrophobic amino acid is to be extracted and separated from a mixture of amino acids, a density of amino acids of up to 30 g/dl can be preferable with regard to the possible maximum load. However, the optimum conditions for the operation must be determined on the basis of the separation pattern of the amino acids to be separated, since the separability tends to become lower with the increase of the load.

The invention now being generally described, the same will be better understood by reference to certain specific examples which are included herein for purposes of illustration only and are not intended to be limiting of the invention or any embodiment thereof, unless specified.

EXAMPLE

EXAMPLE 1

An aqueous solution of a mixture of amino acids having the composition set forth below was subjected to centrifugal liquid-liquid partition chromatography under the following operational conditions, using a liquid-liquid partition chromatography system (Model IMF-001) manufactured by Sanki Engineering Co., Ltd.

Results obtained were as shown in FIG. 1

As is apparent from the above description, the present invention makes it possible to separate leucine in a commercially advantageous manner from a mixture of amino acids containing both leucine and isoleucine. Accordingly, this invention is highly useful in an industrial setting.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for separating leucine from a mixture of amino acids containing at least leucine and isoleucine, which comprises subjecting an aqueous solution of a mixture of amino acids to centrifugal force, and forcing by the application of pressure a water-saturated organic solvent immiscible with water to pass through the aqueous solution against the centrifugal force, to selectively extract leucine in said water-saturated organic solvent.

2. A method for separating leucine as defined in claim 1, wherein the content of isoleucine contained in the amino acids extracted with said organic solvent is 2% or less.

3. A method for separating leucine as defined in claim 1, wherein the pH of the said aqueous solution is in the range of from 1 to 3.

4. A method for separating leucine as defined in claim 1, wherein said organic solvent is an alcohol containing from 3 to 4 carbon atoms.

| | Conditions of Experiment | |
|---|---|---|
| Composition of Partition Liquid | Normal Elution | Reverse Elution |
| n-Butanol 1 | Stationary Phase: Lower layer | Liquid Supply Rate: 2.1 kg/cm$^2$ |
| Water 1 | Mobile Phase: Upper layer (Ascending method) | |
| Cartridge: Type 250 W Number 12 | Liquid Supply Rate: 2.1 ml/min. | Liquid Supplying Pressure: 24 kg/cm$^2$ |
| Quantity of Sample: 1 ml | Liquid Supplying Pressure: 44 kg/cm$^2$ | Number of Rotations: 600 rpm |
| | Flow out of Stationary Phase: 86 ml | |
| Operational Temperature: 25° C. | Number of Rotations: 600 rpm | 1 Fraction: 1 min., 2.1 ml |
| Detection: Amino Acid Analyzer | 1 Fraction: 3 min., 6.3 ml Total Volume Eluted: 787.5 ml | Total Volume Eluted: 262.5 ml |

Composition of the Sample

| | |
|---|---|
| Ile: 1.6 g/dl | |
| Leu: 4.8 g/dl | pH = 1.8 (HCl) |

Analysis

Model 835 Amino Acid Analyser manufactured by Hitachi Ltd.
Ninhydrin method

UNITED STATES PATENT AND TRADEMARK OFFICE
CERTIFICATE OF CORRECTION

PATENT NO. : 4,820,869
DATED : April 11, 1989
INVENTOR(S) : Masaru Otani et al.

It is certified that error appears in the above-identified patent and that said Letters Patent is hereby corrected as shown below:

Column 2, line 41, delete "phasae" and insert

--phase--.

Signed and Sealed this

Third Day of July, 1990

Attest:

HARRY F. MANBECK, JR.

*Attesting Officer*     Commissioner of Patents and Trademarks